United States Patent [19]

Speckmann

[11] Patent Number: 4,820,158

[45] Date of Patent: Apr. 11, 1989

[54] DEVICE FOR COUPLING DENTURES TO TOOTH CROWNS

[75] Inventor: Frank Speckmann, Hagen, Fed. Rep. of Germany

[73] Assignee: Nova-Pro Attachment GmbH, Meinerzhagen, Fed. Rep. of Germany

[21] Appl. No.: 216,321

[22] Filed: Jul. 7, 1988

[30] Foreign Application Priority Data

Jul. 7, 1987 [DE] Fed. Rep. of Germany ....... 3722326

[51] Int. Cl.[4] ........................................... A61C 13/225
[52] U.S. Cl. ..................................... 433/182; 433/181
[58] Field of Search ................. 433/180, 181, 182, 183

[56] References Cited

U.S. PATENT DOCUMENTS

| 2,694,858 | 11/1954 | Cluytens | 433/182 |
| 3,117,377 | 1/1964 | Poveromo | 433/182 |
| 3,710,446 | 1/1973 | Poveromo | 433/182 |

FOREIGN PATENT DOCUMENTS

| 3339084 | 5/1985 | Fed. Rep. of Germany | 433/182 |
| 8517420 | 9/1985 | Fed. Rep. of Germany | 433/182 |
| 3515819 | 1/1986 | Fed. Rep. of Germany | 433/181 |
| 1493268 | 9/1966 | France | 433/182 |
| 528260 | 11/1972 | Switzerland | 433/182 |

*Primary Examiner*—John J. Wilson
*Attorney, Agent, or Firm*—Peter K. Kontler

[57] ABSTRACT

A denture can be coupled to a sleeve-like socket of a tooth crown by a dentent member a first portion of which is anchored in the denture and a sleeve-like second portion of which is receivable in the socket. The second portion has an open end which is remote from the first portion, a conical internal surface which diverges in a direction toward the open end and a conical external surface which diverges in a direction away from the open end. The detent member is made of a tough and wear-resistant plastic material, such as a fiber-reinforced polyamide or polycarbonate. The shank of a screw is driven into a tapped bore of the first portion of the detent member and the head of the screw has a conical outer surface which can expand the second portion of the detent member in response to rotation of the screw so that the head is driven into the second portion by way of the open end. This causes the external surface of the second portion to bear against the internal surface of the socket with a force which can be varied within a desired range by rotating the screw.

12 Claims, 3 Drawing Sheets

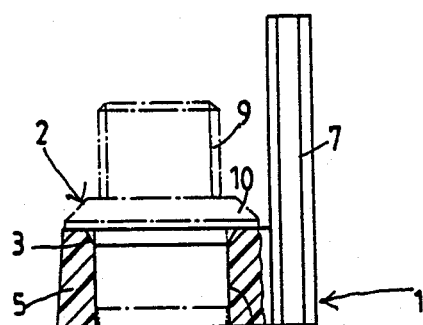
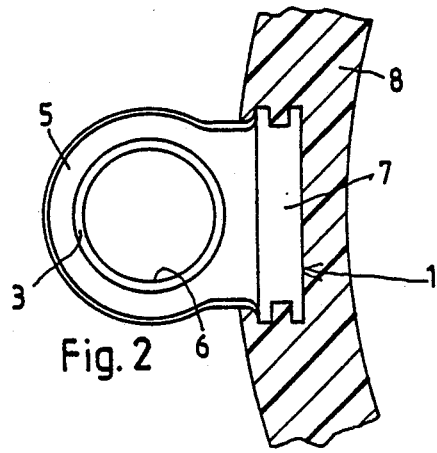
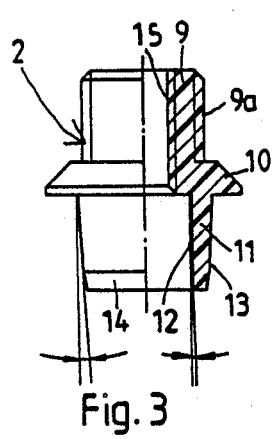
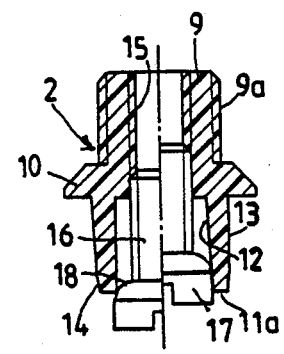

DEVICE FOR COUPLING DENTURES TO TOOTH CROWNS

BACKGROUND OF THE INVENTION

The invention relates to improvements in devices for coupling dentures to natural teeth, and more particularly to improvements in devices for separably coupling bridges, prostheses and other types of dentures to artificial or non-artificial crowns of natural teeth.

German Utility Model No. 85 17 420 of Janzen discloses a coupling device wherein a sleeve-like male detent member which is attached to the denture can be separably inserted into a socket on a crown by means of a screw which can be driven into the detent member. The latter is slotted and is made of a resilient metallic material which is subject to extensive wear. Moreover, it is not possible to correct the orientation of an improperly oriented detent member. Still further, the cost of the coupling device is very high because the socket must be soldered to the crown. The cost of replacing a damaged or broken part of the coupling device is also very high.

Coupling devices which are similar to the coupling device of Janzen are disclosed in Swiss Pat. No. 528 260 to Guglielmetti and in German Offenlegungsschrift No. 33 39 084 of Veit.

German Offenlegungsschrift No. 35 15 819 of Sulc discloses a coupling device wherein the male detent member is releasably held in the socket on a crown by snap action.

French Pat. No. 1,493,268 to Cleveland discloses a male detent member which is slotted and can be expanded by the conical head of a screw so that it bears against the internal surface of a female detent member. The male or female detent member is anchored in the root of a natural tooth.

U.S. Pat. No. 2,694,858 to Cluytens discloses a mounting for artificial teeth wherein the socket on a tooth crown receives a male detent member which is held therein by a screw. An elastic washer surrounds the shank of the screw and is caused to expand against that end face of the socket which is adjacent the head of the screw.

Commonly owned copending patent application Ser. No. 07/214, 756 filed May 16, 1988 discloses a method of providing a tooth crown with a channeled female detent member. This application does not disclose any means for expanding the male detent member which extends into the channel of the female detent member when the crown supports a prosthesis.

OBJECTS AND SUMMARY OF THE INVENTION

An object of the invention is to provide a simple but reliable device which can be used to separably couple a denture to a tooth crown.

Another object of the invention is to provide a coupling device which comprises a small number of simple and inexpensive parts.

A further object of the invention is to provide a novel and improved tooth crown which can be used in conjunction with the above outlined coupling device.

An additional object of the invention is to provide a novel and improved method of making the crown jointly with a part of the coupling device.

Still another object of the invention is to provide a novel and improved detent member for use in the above outlined coupling device.

A further object of the invention is to provide novel and improved means for moving the detent member into engagement with a part of the crown and for selecting the force with which the denture is coupled to the crown.

An additional object of the invention is to provide a coupling device which permits rapid and painless separation of the denture from the crown.

A further object of the invention is to provide a coupling device which can be applied or disengaged by rudimentary tools.

Another object of the invention is to provide a coupling device wherein the parts which are subject to extensive wear can be replaced with fresh parts for use with the remaining part or parts of the coupling device.

One feature of the present invention resides in the provision of a device for separably coupling a denture (this term is intended to embrace bridges, prostheses and all other types of dental restorations) to a tooth crown, particularly to an artificial crown. The improved coupling device comprises a substantially ring-shaped or sleeve-like socket on the crown, and a male detent member having a first portion which is rigid with the denture and a radially expandable sleeve-like second portion which is receivable in the socket. At least the second portion of the male detent member is made of a tough wear-resistant plastic material and has an open end remote from the first portion, a conical internal surface which diverges in a first direction (namely toward the open end), and a conical external surface which diverges in a second direction (namely away from the open end). The coupling device further comprises means for expanding the second portion of the detent member so as to move the external surface into frictional engagement with the socket when the latter receives the second portion of the detent member. The expanding means comprises a deforming element which is insertable into the second portion of the detent member through the open end and has a conical outer surface which diverges in the first direction and has a maximum diameter greater than the maximum diameter of the internal surface in unexpanded condition of the second portion of the detent member so that the second portion expands radially and moves its external surface into frictional engagement with the socket in response to insertion of the deforming element into the second portion of the detent member. The expanding means preferably further comprises an externally threaded shank which is rigid with the deforming element and can be driven into a tapped hole of the first portion of the detent member. The second portion of the detent member preferably consists of a shape-retaining material which need not exhibit a high degree of elasticity and can be practically non-elastic. For example, the second portion of the detent member can be made of polyamide or polycarbonate and such material can be reinforced by glass fibers or the like.

The difference between the maximum diameters of the internal and outer surfaces preferably exceeds (for example it is approximately or exactly twice) the difference between the minimum and maximum diameters of the external surface.

The taper of the rear portion of the external surface (such rear portion is remote from the open end of the second portion of the detent member) is preferably less pronounced than the taper of the relatively short front portion which is immediately adjacent the open end. This facilitates introduction of the second portion of the detent member into the socket. Such introduction is even more convenient if the inlet end of the socket is surrounded by a substantially conical internal surface of the socket so that such inlet end forms a funnel for introduction of the open end of the second portion of the detent member. The conical internal surface of the socket diverges in a direction away from the other end of the socket, namely in the second direction.

The socket preferably consists of a castable metallic material.

Another feature of the invention resides in the provision of a method of making the tooth crown and the socket. Such method comprises the steps of making an insert which consists of combustible material (preferably at least in part of a totally combustible material) and is an exact replica of the crown and its socket, introducing the insert into a mold and surrounding the introduced insert with sand or other suitable molding material, combusting the insert so that the latter leaves in the molding material a cavity which is complementary to the tooth crown and its socket, and filling the cavity with a castable metallic substance to thus form the crown and the socket.

The novel features which are considered as characteristic of the invention are set forth in particular in the appended claims. The improved coupling device itself, however, both as to its construction and the mode of utilizing the same, together with additional features and advantages thereof, will be best understood upon perusal of the following detailed description of certain specific embodiments with reference to the accompanying drawing.

BRIEF DESCRIPTION OF THE DRAWING

FIG. 1 is a fragmentary sectional view of an insert which is a replica of a tooth crown and its socket, the male detent member being indicated by phantom lines;

FIG. 2 is a plan view of a portion of the replica of the tooth crown and its socket;

FIG. 3 is a partly elevational and partly axial sectional view of the male detent member;

FIG. 4 is an axial sectional view of the male detent member and an elevational view of the expanding means, the latter being shown in two different positions;

DESCRIPTION OF PREFERRED EMBODIMENTS

Figure 5:
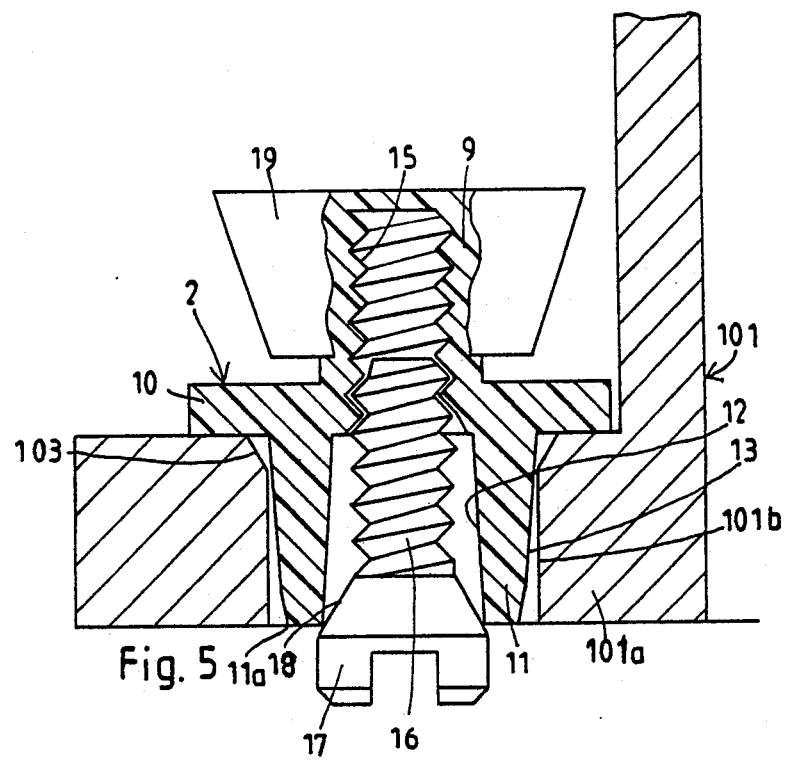
FIG. 5 is an enlarged sectional view of the tooth crown and its socket, and further showing the male detent member, a portion of the denture and the expanding means in a first position prior to deformation of the second portion of the male detent member.

FIGS. 1 and 2 show a portion of an insert which is made of a combustible material and is an exact replica of an artificial tooth crown and a ring-shaped or sleeve-like socket. The replica of the socket is shown at 5, and a portion of the replica of the crown is shown at 8. The preferably totally combustible material of the replica 5 can be a suitable plastic substance such as polyamide or polycarbonate. The replica 5 of the socket has a cylindrical hole 6 with an outwardly tapering conical internal surface 3 at one end. The surface 3 diverges in a direction away from the other end of the hole 6. The socket-like replica 5 is integral with a profiled extension 7 which is embedded in a complementary recess 1 of the replica 8 of the crown. The material of the replica 8 may but need not be identical with the material of the replica 5. For example, the replica 8 can be made of wax.

In order to make a crown 101 (FIGS. 5 to 7), the dentist or his technician first makes the replica 5 and its extension 7 from a totally combustible material. The replica 8 of the crown is made in a separate step and is provided with the recess 1 for the extension 7. The combined replica (5+8) of the socket 101a (FIGS. 5-6) and crown 101 is then placed into a mold 30 (see FIG. 8), and the mold is filled with sand or other suitable molding material 31 which fills the hole 6 of the replica 5 as well as the interior of the replica 8 and completely surrounds the parts 5 and 8. A suitable parallel mechanism can be used to properly orient the replica 5 relative to the replica 8 prior to introduction of the combined replica (5+8) into the mold 30. In the next step, the material of the replicas 5 and 8 is combusted so that the replicas leave in the mold 30 a cavity which is exactly complementary to the crown 101 and its socket 101a. The cavity is filled with a castable metallic material which is permitted to set and thus constitutes a metallic crown 101 with an integral socket 101a.

The improved coupling device comprises the socket 101a and a male detent member 2 which is indicated by phantom lines in FIG. 1 and all details of which are shown in FIGS. 3 to 7. The detent member 2 is preferably made of a tough and highly wear-resistant plastic material, such as a polyamide or a polycarbonate which can be reinforced by glass fibers or in another suitable way. The detent member 2 can be mass-produced in an injection molding machine and it preferably exhibits a limited amount of elasticity so that it tends to reassume its original shape in response to termination of the application of a deforming stress.

Figure 6:
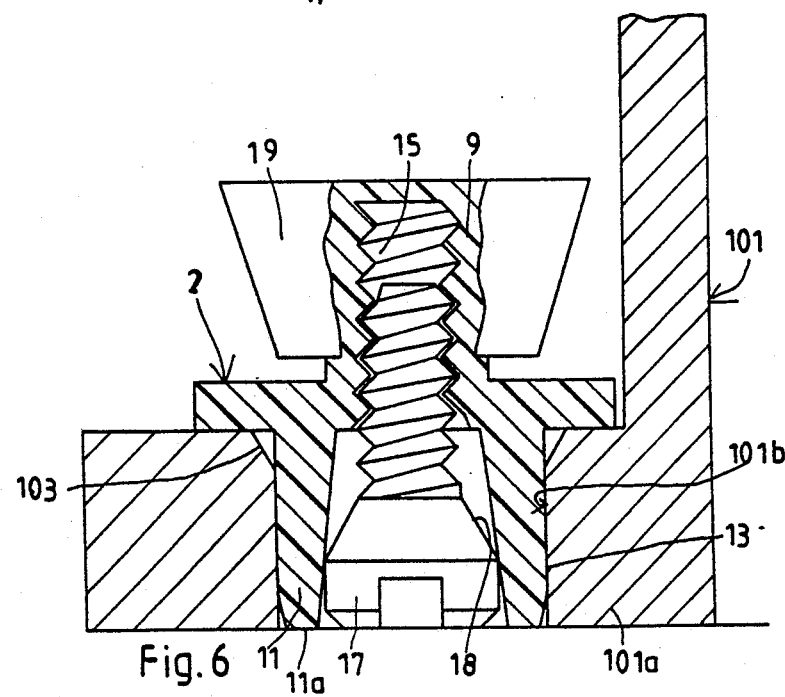
FIG. 6 shows the structure of FIG. 5 but with the deforming element of the expanding means in a different position.
Figure 7:
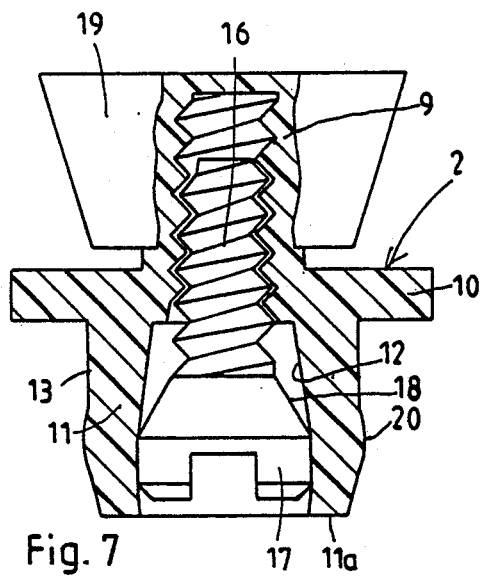
FIG. 7 shows a portion of the structure of FIGS. 5 and 6 but with the deforming element in a third position.
Figure 8:
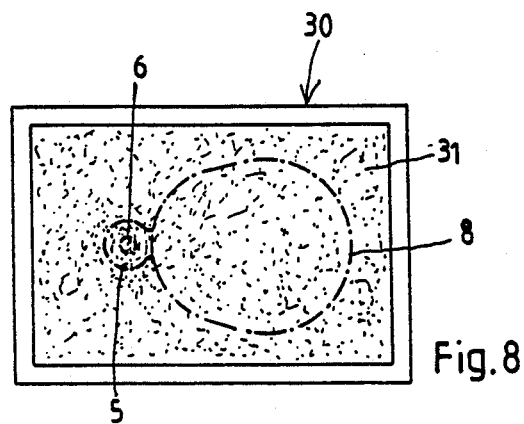
FIG. 8 is a schematic plan view of a mold which can be used for the making of the crown and its socket.

The detent member 2 comprises a first portion 9 which has a tapped hole 15 and is further provided with an external thread 9a so that it can be reliably anchored in the tapped bore or hole of a denture. FIGS. 5 to 7 show a nut 19 which can be said to form a component part of a denture and mates with the first portion 9 of the detent member 2. The latter further comprises a hollow sleeve-like second portion 11 and an intermediate portion 10 which constitutes a collar and determines the extent to which the first portion 9 can be driven into the nut 19. Furthermore, the collar 10 determines the extent to which the second portion 11 of the detent member 2 can be introduced into the socket 101a of the crown 101 when the denture including the nut 19 is to be separably coupled to the crown 101. When the coupling device is assembled, the collar 10 overlies that (funnel-shaped) end of the socket 101a which is formed with a conical internal surface 103 corresponding to the internal surface 3 of the replica 5 shown in FIGS. 1 and 2.

The second portion 11 of the detent member 2 has an open end 11a which is remote from the first portion 9, a conical internal surface 12 which diverges in a direction from the first portion 9 toward the open end 11a, and a conical external surface 13 which diverges in the opposite direction, i.e., from the open end 11a toward the first portion 9. The major (rear) portion of the conical external surface 13 tapers gradually from the collar 10 toward but short of the open end 11a. The remaining (front) portion 14 of the external surface 13 is much shorter than the rear portion and its taper (conicity) is more pronounced so as to facilitate insertion of the open end 11a of the second portion 11 into the socket 101a by way of the funnel-shaped end of the socket.

The coupling device further comprises means for expanding the second portion 11 of the detent member 2 into frictional engagement with the internal surface 101b of the socket 101a on the crown 101. The expanding means comprises a deforming element 17 and an externally threaded shank 16 which can be introduced into the tapped hole 15 of the first portion 9 of the detent member 2. The deforming element 17 can be said to constitute the specially shaped head of a screw whose shank 16 can cause the deforming element to move axially toward or away from the collar 10 whereby the conical outer surface 18 of the deforming element or head 17 expands the second portion 11 of the detent member 2 radially and into engagement with the internal surface 101b of the socket 101a when the portion 11 is properly received in the socket. The maximum diameter of the conical outer surface 18 exceeds the maximum diameter of the conical internal surface 12 in undeformed (i.e., unexpanded) condition of the second portion 11. This can be seen in the left-hand portion of FIG. 4 and in FIG. 5. The dimensions of the second portion 11 and of the deforming element or head 17 are preferably selected in such a way that the difference between the maximum diameters of the surfaces 12 and 18 exceeds (and is preferably approximately or exactly twice) the difference between the maximum and minimum diameters of the conical external surface 13. When used in this specification, the terms "taper" and "conicity" denote the difference between the maximum and minimum radii or diameters of the respective conical surfaces.

The left-hand portion of FIG. 4 shows that, before the second portion 11 of the detent member 2 is expanded, the smaller-diameter portion of the conical outer surface 18 of the deforming element 17 extends into but the larger-diameter portion of this conical outer surface is located outside of the second portion 11. If the expanding means (16+17) is thereupon rotated in a direction to drive the shank 16 deeper into the tapped hole 15 of the first portion 9 of the detent member 2, the conical outer surface 18 expands the sleeve-like second portion 11 in the region of the open end 11a beyond the elastic limit and the deforming element 17 is clamped in the portion 11 so that it cannot readily change its angular and axial positions relative to the detent member 2. Furthermore, the deforming element 17 then causes the conical external surface 13 to assume the shape of, or to closely resemble, a cylindrical surface. This is due to the aforediscussed selection of the ratio of the difference between the maximum diameters of the conical surfaces 12, 16 to the difference between the maximum and minimum diameters of the conical external surface 13. At the same time, the deforming element 17 increases the conicity of the internal surface 12. This can be seen in the right-hand portion of FIG. 4. If the person in charge continues to turn the expanding means 17+18 in a direction to drive the deforming element 17 deeper into the sleeve-like second portion 11 of the detent member 2, the localized expansion of the portion 11 increases and the portion 11 engages the internal surface 101b of the socket 101a with a greater force. As can be seen in FIG. 7, the deforming portion 17 can cause the sleeve-like portion 11 to assume a shape which resembles that of a barrel (as at 20) because a portion of the external conical surface 13 is compelled to assume a convex shape in the region radially outwardly of the cylindrical portion of the deforming element 17. This is attributable to the aforediscussed selection of conicity or taper of the surfaces 12, 13 and 18. The dentist can select any one of a practically infinite number of different forces which retain the second portion 11 of the detent member 2 in the socket 101a, i.e., which couple the denture including the nut 19 to the crown 101. The adjustment can be carried out as frequently as necessary. If the wear on the second portion 11 of the detent member 2 and/or upon the expanding means 16+17 is extensive or excessive, the corresponding part is simply replaced with a fresh part to thus ensure that the person in charge can couple the denture to the crown with a desired force.

Introduction of the second portion 11 into the socket 101a is facilitated by the front portion 14 of the conical external surface 13 as well as by the conical internal surface 103 of the socket 101a.

FIG. 5 shows the initial stage of coupling the nut 19 (i.e., the denture) to the crown 101. The shank 16 of the expanding means extends into the tapped hole 15 but the larger-diameter portion of the conical outer surface 18 is still outside the sleeve-like portion 11 so that the external surface 13 need not even contact the surface 101b which surrounds the cylindrical portion of the hole in the socket 101a. This permits convenient insertion of the sleeve-like portion 11 into or its extraction from the socket 101a. The nut 19 is assumed to be embedded into the material of the denture (e.g., a bridge or a prosthesis with one or more artificial teeth).

If the shank 16 is thereupon caused to move axially so as to draw the conical outer surface 18 deeper into the sleeve-like portion 11, the latter undergoes radial expansion and its formerly conical external surface 13 assumes the shape of a cylinder and lies flush against the adjacent portion of the cylindrical internal surface 101b of the socket 101a. This is shown in FIG. 6. At such time, at least a portion of the cylindrical part of the deforming element 17 is already located in the interior of the portion 11. If the frictional engagement between the external surface 13 and the socket 101a suffices to ensure reliable retention of the denture in a selected position with reference to the crown 101, the shank 16 is left in the axial position of FIG. 6. If it is desired or necessary to establish an even more pronounced frictional engagement, the deforming element is rotated again and the shank 16 assumes the axial position of FIG. 7 in which the cylindrical portion of the deforming element 17 imparts to the surrounding part of the sleeve-like portion 11 the shape of a barrel (as at 20) with the result that such barrel-shaped part engages the socket (not shown in FIG. 7) with an even greater force. As mentioned above, the retaining force can be varied infinitely between a relatively low value and a much higher value.

An advantage of the improved coupling device is that its socket 101a is an integral part of the crown 101. This ensures that the orientation of the socket 101a cannot change as long as the crown 101 is in place. Moreover, the socket 101a can stand very long periods of use because it is made of the same strongly wear resistant material (normally a noble metal) as the crown 101.

Another important advantage of the improved coupling device is that the force with which the detent member 2 engages the socket 101a can be selected and varied practically at will. Moreover, and since the detent member 2 is made of a strongly wear-resistant material, its useful life is very long. Still further, and since the frictional engagement between the detent member 2 and the socket 101a can be terminated in an extremely simple way, a damaged or worn detent member can be rapidly replaced with a fresh detent member which is simply anchored in the nut 19 of the denture and is thereupon coupled with the socket 101a in the aforediscussed manner to thus establish a separable connection without any undesirable play. The aforediscussed presently preferred material of the detent member 2 further ensures that the selected axial and angular positions of the expanding means 16+17 remain unchanged unless an authorized and competent person decides that the position of the expanding means must be changed. The conical outer surface 18 of the deforming element 17 renders it possible to expand the entire sleeve-like portion 11 into strong frictional engagement with the socket 101a while simultaneously enabling selected portions of the external surface 13 to even more strongly engage the adjacent portions of the cylindrical surface 101b in the socket 101a (note the barrel-shaped portion 20 in FIG. 7). As a rule, the external surface 13 of the sleeve-like portion 11 is converted into a cylinder shortly after the expansion of the portion 11 in the region of the open end 11a begins so that the entire portion 11 is put to use as a means for frictionally holding the detent member 2 in satisfactory engagement with the socket 101a.

The feature that the originally conical external surface 13 of the sleeve-like portion 11 assumes the shape of a cylinder shortly after the deforming element 17 begins to expand the portion 11 in the region of the open end 11a is attributable, at least in part, to the aforediscussed selection of the ratio of difference between the maximum diameters of the conical surfaces 12, 18 to the difference between the maximum and minimum diameters of the surface 13 (in the undeformed condition of the portion 11).

The conical front end portion 14 of the conical external surface 13 of the sleeve-like portion 11 cooperates with the conical internal surface 103 of the socket 101a to ensure convenient and rapid insertion of the portion 11 into the socket 101a, even if the denture and the detent member 2 are not maintained in optimum positions for such introduction. The surfaces 14 and 103 steer the sleeve-like portion 11 into the socket 101a even if the person in charge cannot observe the socket and the detent member during coupling of the denture to the crown 101. The surfaces 14 and 103 thus reduce the likelihood of damage to the crown, to the denture and/or to the coupling device during insertion of the denture and they reduce the likelihood of causing pain to the patient.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A device for separably coupling a denture to a tooth crown, comprising a substantially ring-shaped socket on the crown; a male detent member having a first portion rigid with the denture and a radially expandable sleeve-like second portion receivable in said socket, at least said second portion consisting of a tough wear-resistant plastic material and having an open end, a conical internal surface which diverges in a first direction toward said open end and a conical external surface which diverges in a second direction away from said open end; and means for expanding said second portion so as to move said external surface into frictional engagement with said socket when the latter receives said second portion, said expanding means comprising a deforming element insertable into said second portion through said open end and having a conical outer surface which diverges in said first direction and has a maximum diameter greater than the maximum diameter of said internal surface in unexpanded condition of said second portion so that the second portion expands radially and moves said external surface against the socket in response to insertion of the deforming element into said second portion.

2. The device of claim 1, wherein said expanding means further comprises an externally threaded shank and said first portion has a tapped hole for said shank.

3. The device of claim 1, wherein said second portion consists of a shape-retaining material.

4. The device of claim 1, wherein the difference between the maximum diameters of said internal and outer surfaces exceeds the difference between the maximum and minimum diameters of said external surface.

5. The device of claim 4, wherein the difference between the maximum diameters of said internal and outer surfaces is approximately twice the difference between the maximum and minimum diameters of said external surface.

6. The device of claim 1, wherein said external surface has a rear portion remote from and a front portion adjacent said open end, the conicity of said front portion exceeding the conicity of said rear portion.

7. The device of claim 6, wherein the axial length of said front portion is a fraction of the axial length of said rear portion.

8. The device of claim 1, wherein said socket has an inlet end for introduction of said second portion thereinto, a second end, and a substantially conical surface surrounding said inlet end and diverging in a direction away from said second end.

9. The device of claim 8, wherein the conicity of the conical surface of said socket exceeds the conicity of said external surface.

10. The device of claim 1, wherein said socket consists of a castable metallic material.

11. The device of claim 1, wherein the material of said second portion is selected from the group consisting of polyamides and polycarbonates.

12. The device of claim 1, wherein said second portion consists of a fiber-reinforced material.

* * * * *